US011373453B2

(12) United States Patent
Young et al.

(10) Patent No.: US 11,373,453 B2
(45) Date of Patent: Jun. 28, 2022

(54) METHOD AND SYSTEM TO SECURELY REGISTER A USER IN A BIOMETRIC SYSTEM

(71) Applicant: Konica Minolta Business Solutions U.S.A., Inc., Ramsey, NJ (US)

(72) Inventors: Kenneth Huang Young, San Mateo, CA (US); Randy Cruz Soriano, San Leandro, CA (US); Yu-Shing Chen, Cupertino, CA (US); Ann Qiongying Feng, San Jose, CA (US)

(73) Assignee: KONICA MINOLTA BUSINESS SOLUTIONS U.S.A., INC., Ramsey, NJ (US)

(*) Notice: Subject to any disclaimer, the term of this patent is extended or adjusted under 35 U.S.C. 154(b) by 274 days.

(21) Appl. No.: 16/835,384

(22) Filed: Mar. 31, 2020

(65) Prior Publication Data

US 2021/0303892 A1    Sep. 30, 2021

(51) Int. Cl.
| | |
|---|---|
| G06F 21/32 | (2013.01) |
| G06F 21/40 | (2013.01) |
| G06F 21/44 | (2013.01) |
| H04W 4/80 | (2018.01) |
| A61B 5/024 | (2006.01) |
| G06V 40/50 | (2022.01) |
| G01S 19/25 | (2010.01) |
| H04W 4/021 | (2018.01) |
| G06F 21/62 | (2013.01) |

(52) U.S. Cl.
CPC .......... *G06V 40/50* (2022.01); *A61B 5/02438* (2013.01); *G01S 19/252* (2013.01); *G06F 21/32* (2013.01); *G06F 21/40* (2013.01); *G06F 21/44* (2013.01); *G06F 21/6272* (2013.01); *H04W 4/021* (2013.01); *H04W 4/80* (2018.02)

(58) Field of Classification Search
CPC . A61B 5/02438; A61B 5/1172; A61B 5/1176; G01S 19/252; G06F 21/32; G06F 21/40; G06F 21/44; G06F 21/6272; G06F 2221/2117; G06V 40/50; H04W 4/021; H04W 4/80
See application file for complete search history.

(56) References Cited

U.S. PATENT DOCUMENTS

| | | | |
|---|---|---|---|
| 2017/0193276 A1* | 7/2017 | Choi | G06F 21/32 |
| 2019/0043281 A1* | 2/2019 | Aman | H04W 4/029 |
| 2021/0099441 A1* | 4/2021 | Suraparaju | H04L 63/0861 |

* cited by examiner

*Primary Examiner* — David Bilodeau
(74) *Attorney, Agent, or Firm* — Buchanan Ingersoll & Rooney PC (57) ABSTRACT

A method and system for securely registering a user in a biometric system. The method includes: receiving, on a computer processor of the biometric system, an identifier of a biometric device and user information; sending, with the computer processor, a request that the biometric device be sent to the user of the biometric device upon the receipt of the identifier of the biometric device and user information; receiving, on the computer processor, the identifier of the biometric device and one or more authenticators from the user; initiating, with the computer processor, a registration of the user based on the receipt of the identifier of the biometric device and the one or more authenticators from the user; and receiving, on the computer processor, biometric data of the user from the biometric device to complete a registration of the user in the biometric system.

20 Claims, 8 Drawing Sheets

METHOD AND SYSTEM TO SECURELY REGISTER A USER IN A BIOMETRIC SYSTEM

TECHNICAL FIELD

The present disclosure generally relates to a method and system to securely register a user in a biometric system.

BACKGROUND

In today's implementation of systems that uses a user's biometrics to securely identify him/her, the system would at first need to register the person into the system. After the initial registration is completed, the user may then use his/her biometric data in order to gain access into the system.

However, in a system involving the registration of a user into a biometric system, it is possible that the biometric information of the person is stolen during the process of initial registration between the user and the System.

SUMMARY

In consideration of the above issues, it would be desirable to provide a system and method to securely register a user in a biometric system.

In accordance with an aspect, for securely registering a user in a biometric system, the method comprising: receiving, on a computer processor of the biometric system, an identifier of a biometric device and user information; sending, with the computer processor, a request that the biometric device be sent to the user of the biometric device upon the receipt of the identifier of the biometric device and user information; receiving, on the computer processor, the identifier of the biometric device and one or more authenticators from the user; initiating, with the computer processor, a registration of the user based on the receipt of the identifier of the biometric device and the one or more authenticators from the user; and receiving, on the computer processor, biometric data of the user from the biometric device to complete a registration of the user in the biometric system.

In accordance with another aspect, a non-transitory computer readable medium storing computer readable program code executed by a processor for securely registering a user in a biometric system is disclosed, the process comprising: receiving, on a computer processor of the biometric system, an identifier of a biometric device and user information; sending, with the computer processor, a request that the biometric device be sent to the user of the biometric device upon the receipt of the identifier of the biometric device and user information; receiving, on the computer processor, the identifier of the biometric device and one or more authenticators from the user; initiating, with the computer processor, a registration of the user based on the receipt of the identifier of the biometric device and the one or more authenticators from the user; and receiving, on the computer processor, biometric data of the user from the biometric device to complete a registration of the user in the biometric system.

In accordance with a further aspect, a system is disclosed for securely registering a user in a biometric system, the system comprising: a biometric device; a computer processor of the biometric system, the computer processor configured to: receive an identifier of the biometric device and user information; send a request that the biometric device be sent to the user of the biometric device upon the receipt of the identifier of the biometric device and user information; receive the identifier of the biometric device and one or more authenticators from the user; initiate a registration of the user based on the receipt of the identifier of the biometric device and the one or more authenticators from the user; and receive biometric data of the user from the biometric device to complete a registration of the user in the biometric system.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION

Reference will now be made in detail to the present preferred embodiments of the invention, examples of which are illustrated in the accompanying drawings. Wherever possible, the same reference numbers are used in the drawings and the description to refer to the same or like parts.

Figure 1:
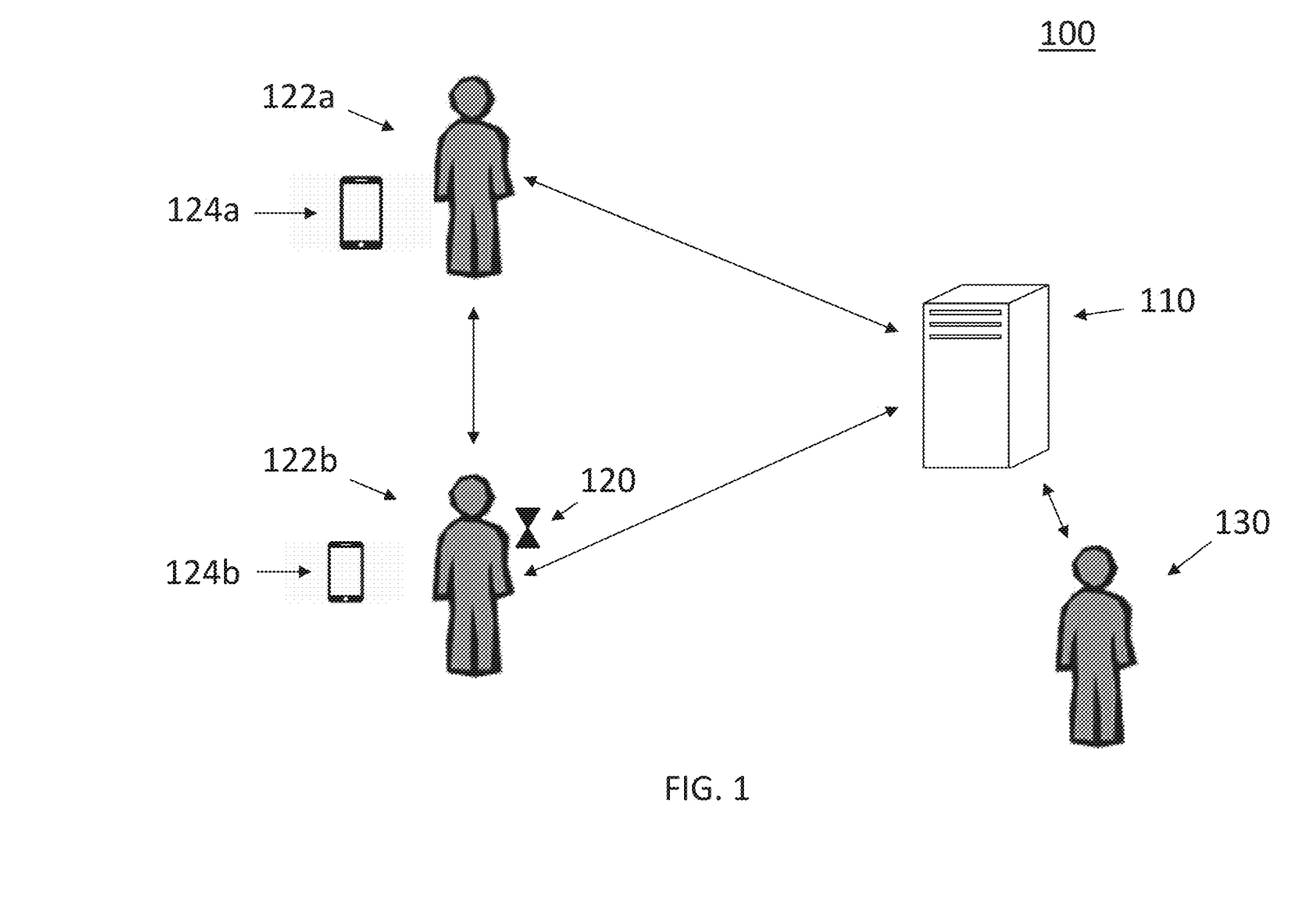
FIG. 1 is an illustration of a system to securely register a user in a biometric system in accordance with an exemplary embodiment.

FIG. 1 is an illustration of a system 100 to securely register a user in a biometric system in accordance with an exemplary embodiment. As shown in FIG. 1, the system 100 can include a biometric system (i.e., computer processor) 110 and one or more biometric devices 120 in accordance with an exemplary embodiment. In accordance with an exemplary embodiment, it would be desirable to have a method and system in which, for example, an intended user 122b of the biometric device 120 can be securely registered into the biometric system 110.

In accordance with an embodiment, the system 100 can include an administrator 122a of the biometric system 100, and the user 112b, the user being a person who wishes to register himself into the biometric system 110 so that all future access into the biometric system 110 is allowed using the user's biometric data. In accordance with an exemplary embodiment, the biometric system 110, can be the actual hardware and/or software associated with a computer, badge readers, Iris scanners, fingerprint readers or any device that will read biometric information to gain access. For example, the compute system 110 may have back-end server software that can perform the actual processing of biometric data. The reading/scanning device together with the back-end server software can be defined as the computer system.

In accordance with an exemplary embodiment, the biometric device 120 of the user 122b may communicate with a client 124b, for example, a mobile client, tablet, or personal computer, when Bluetooth or Near Field Communication (NFC) or other protocols are available to transfer and/or receive the biometric data, access codes and/or temporary codes as disclosed herein. For example, the client 124b may include a display unit or graphical user interface, which can access, for example, a web browser in the memory of the mobile client (or mobile device). The mobile client (or mobile device) also includes the operating system (OS), which manages the computer hardware and provides common services for efficient execution of various software programs.

Figure 2:
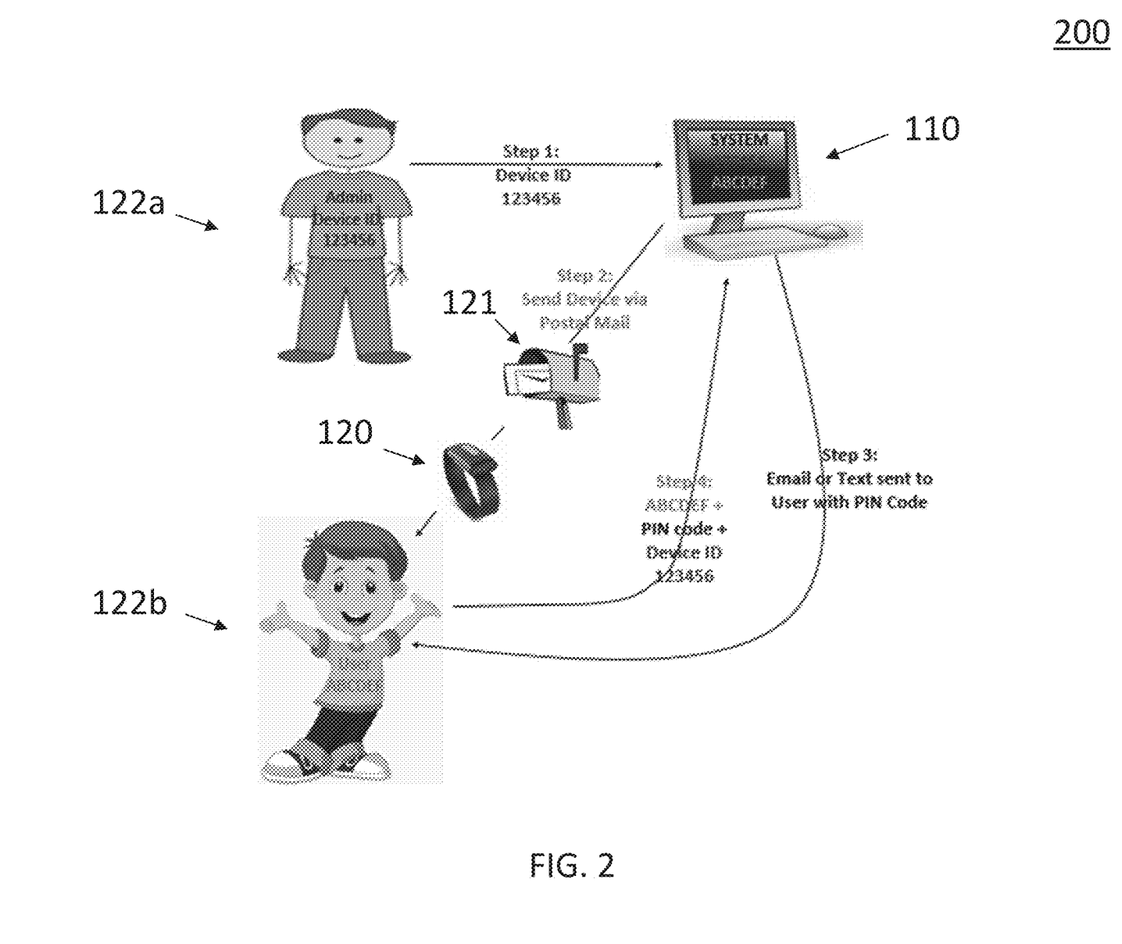
FIG. 2 is an illustration of system for registering a user in a biometric system as currently performed.

FIG. 2 is an illustration of system 200 for registering a user in a biometric system 110 as currently performed. As shown in FIG. 2, the registration process generally requires the user 122b to receive the biometric device 120 together with either an email, a text message or postal mail 121 with accompanying, for example, a personal identification number (i.e., PIN code). As soon as the user 122b receives both the biometric device 120 and the PIN code 121, the user 120 can upload his biometric data (using the device 120) and PIN code 121 to the system 110 in order to register himself/herself.

As shown in FIG. 2, in some cases, the registration process is a 4-step process. In step 1, the administrator enters the user's biometric device identifier (i.e., Device ID 123456) into the biometric system 110. In step 2, the biometric system 110 sends out the biometric device 120 to the user 122b, for via postal mail and/or courier service 121. In step 3, the biometric system 110 sends an email or a text message with the PIN code to the user 122b. In step 4, once the user 122b receives both the biometric device 120 and the PIN code, the user records his/her biometric data ABCDEF. Then, for example, the user 122b sends all three items, the biometric data ABCDEF, the PIN code, and the Device ID 123456 to the biometric system 110. Once all three items are received by the biometric system 110, the biometric system 110 can proceed with the registration or registering of the user 122b.

Figure 3:
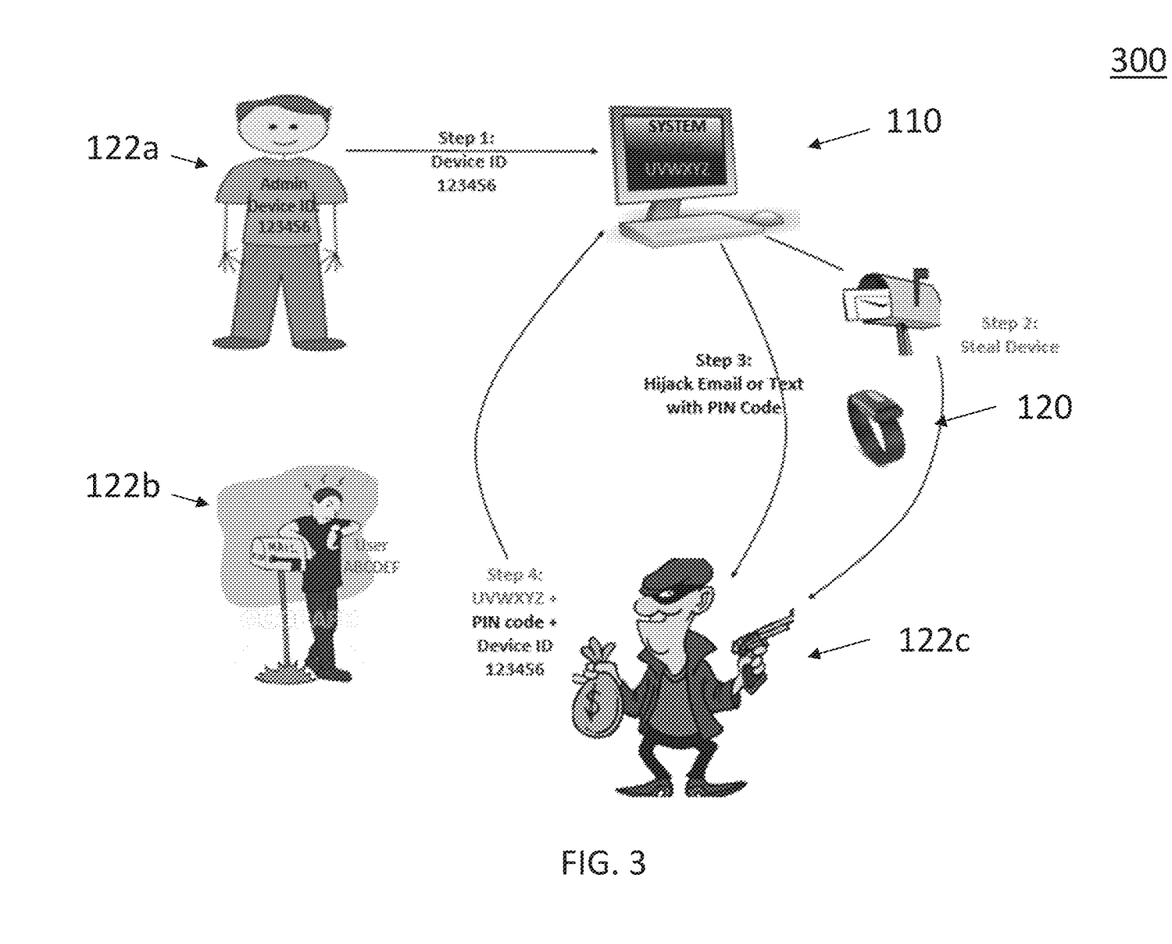
FIG. 3 is an illustration of the system for registering a user in a biometric system when a biometric device is stolen.

FIG. 3 is an illustration of the system 300 for registering a user 122b in a biometric system when a biometric device 120 is stolen. As shown in FIG. 3, one of the problem with the process as disclosed in FIG. 2 is that it is relatively easy for a burglar (i.e., another) 122c to steal the biometric device 120 and hijack the email of the intended user 122b. Once the burglar (i.e., another) 122c gets access to both the biometric device 120 and the PIN code, for example, the burglar 122c can easily pretend to be the intended user 122b. Thus, the present process for registering a user in a biometric system 110 may be compromised.

Figure 4:
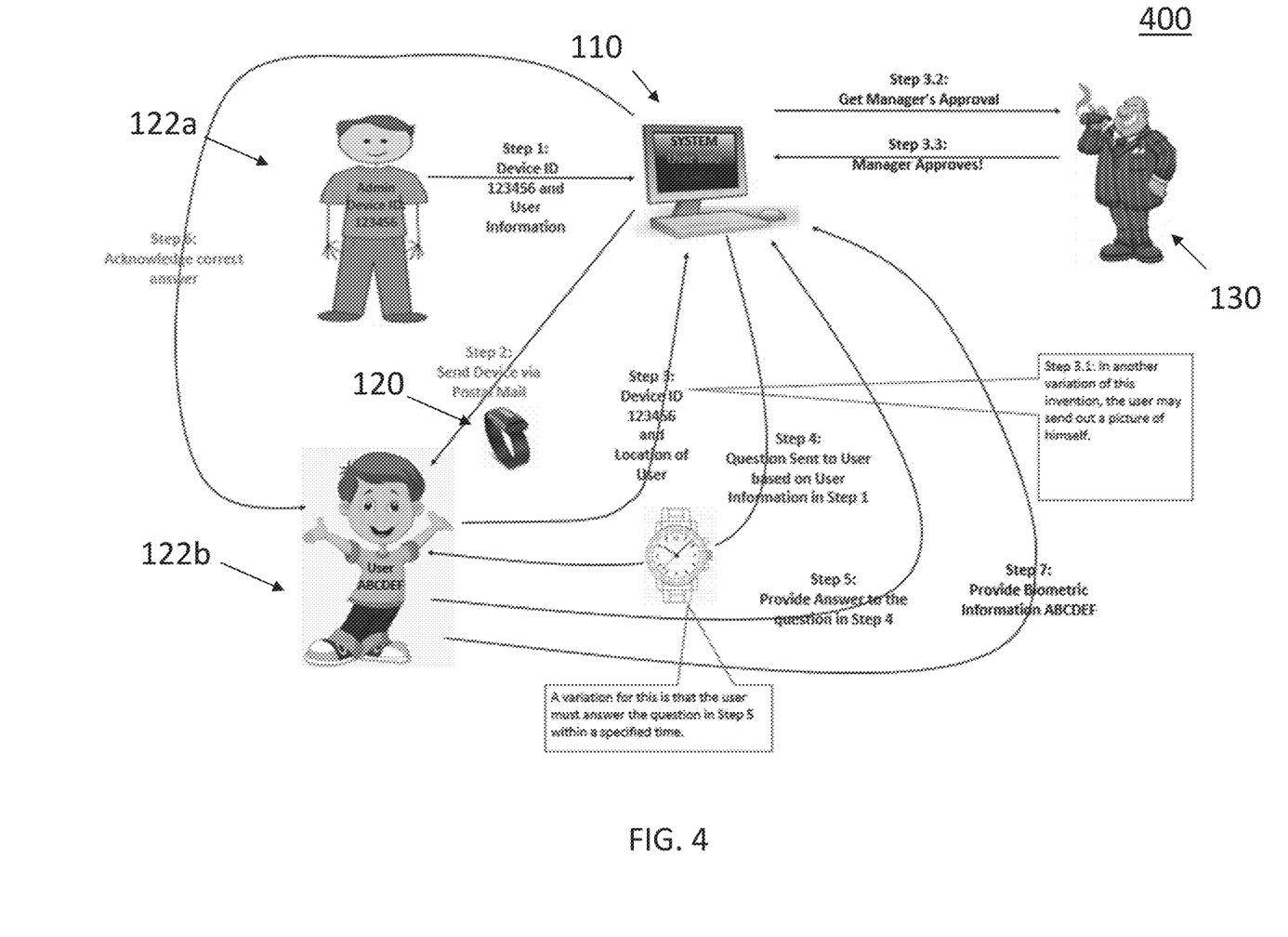
FIG. 4 is an illustration of a system for securely registering a user in biometric system in accordance with an embodiment.

FIG. 4 is an illustration of a system 400 for securely registering a user 122b in a biometric system 110 in accordance with an exemplary embodiment. As shown in FIG. 4, in accordance with an exemplary embodiment the process can include the following steps. In step 1, the administrator 122a enters an ID (identifier) 123456 for the user's biometric device 120 plus information regarding the user 122b (i.e., user information), for example, name, address (i.e., location), phone number, a user ID or employee number, etc., into the biometric system 110. In accordance with an embodiment, the user information can include information that only the user 122b will know. In step 2, the biometric device 120 is sent to the user via, for example, postal mail and/or delivery service. In step 3, upon receiving the biometric device 120, the intended user 122b will send the biometric device ID 123456 plus the location of the user 122b to the biometric system 110. In accordance with an exemplary embodiment, the location of the user 122b must match the address provided by the administrator 122a in step 1 together with the biometric device ID (i.e., 123456).

In accordance with an aspect of the disclosure, the intended user 122b may be requested to send a picture (or digital image) of himself/herself, for example, via a mobile phone 124b. In accordance with an exemplary, the biometric system 110 (i.e., computer system) can, for example, using a pattern recognition or facial recognition program, match the face in the photo (or digital image) with a photograph of the user 122b, which has been entered as part of the user information in step 1. In accordance with an embodiment, if the photograph matches, the process proceed to step 4. Alternatively, in another embodiment, the process can include a further validation, for example, as shown in Step 3.2.

In accordance with another variation of this disclosure, the user may be able to send a picture of himself. Upon receiving the photo, the biometric system 110 can forward it to a supervisor or manager 130 for verification. In accordance with an embodiment, if the supervisor or manager 130 recognizes the employee (i.e., intended user 122b) based on an employee photograph obtained during, for orientation and/or via personal meetings with the employee (i.e., user 122b), and if the intended user 122b is recognizable by the manager 130, then the supervisor or manager 230 can approve the individual in the provided photograph and authorization can be forwarded to the biometric system 110.

In accordance with another embodiment, when different variations of initial validation is performed, for example, in Steps 3, 3.1, 3.2/3.3 and they all match from the known data, the biometric system 110 can generation and send one or more questions to the user 122b based on the user information provided in Step 1. In accordance with an exemplary embodiment, the one or more questions can be random question(s) to the user based on the user information provided in Step 1. For example, in many system with an implementation of asking for a secret question, the user typically sets up the question for the biometric system 110, which questions are used for a later time in which the user is asked for responses to the secret question(s). In accordance with an exemplary embodiment, the secret question is preferably not setup by the user, instead the secret question or questions can be based on information provided, for example, by the administrator 122a, a third-party person associated with this transaction, and/or based on public records obtained, for example, via a machine learning algorithm, for example, addresses and/or cities in which the user has lived in the past.

In accordance with an exemplary embodiment, the process can include one or more variations to the type of questions and/or secret question. For example, in accordance with an embodiment, the intended user 122b can provide the answer(s) to the secret question(s). In another variation of this disclosure, the secret question has to be responded in a relatively short time and/or within a set response time. The biometric system 110 can be configured to acknowledge in Step 6, if the answer(s) in Step 5 matches the information provided in Step 1. If the response to the one or more questions are correct, the biometric system 110 will request that the user 122b begin the registration with the biometric device 120.

In accordance with an exemplary embodiment, the providing of a plurality or plural verifications such as location, photograph recognition using artificial intelligent (AI), photo recognition with assistance of a supervisor or a manager, and/or the random question-answer protocol between the user and the biometric system 110 using information from, for example, a third party can provide a system that is relatively more secure than current systems of registering a user 122b into a biometric system 110 for the first time as shown in FIGS. 2 and 3.

In accordance with an exemplary embodiment, it should be noted that although for explanation purposes that the phrase "send biometric data" is used frequently. In reality, for example, due to security reasons, biometric data is never sent to the system. Instead, the biometric device 120 will use an encryption algorithm, for example, Pubic key infrastructure (PKI) to send the biometric date to the biometric system 110, instead of sending actual biometric data.

Figure 5:
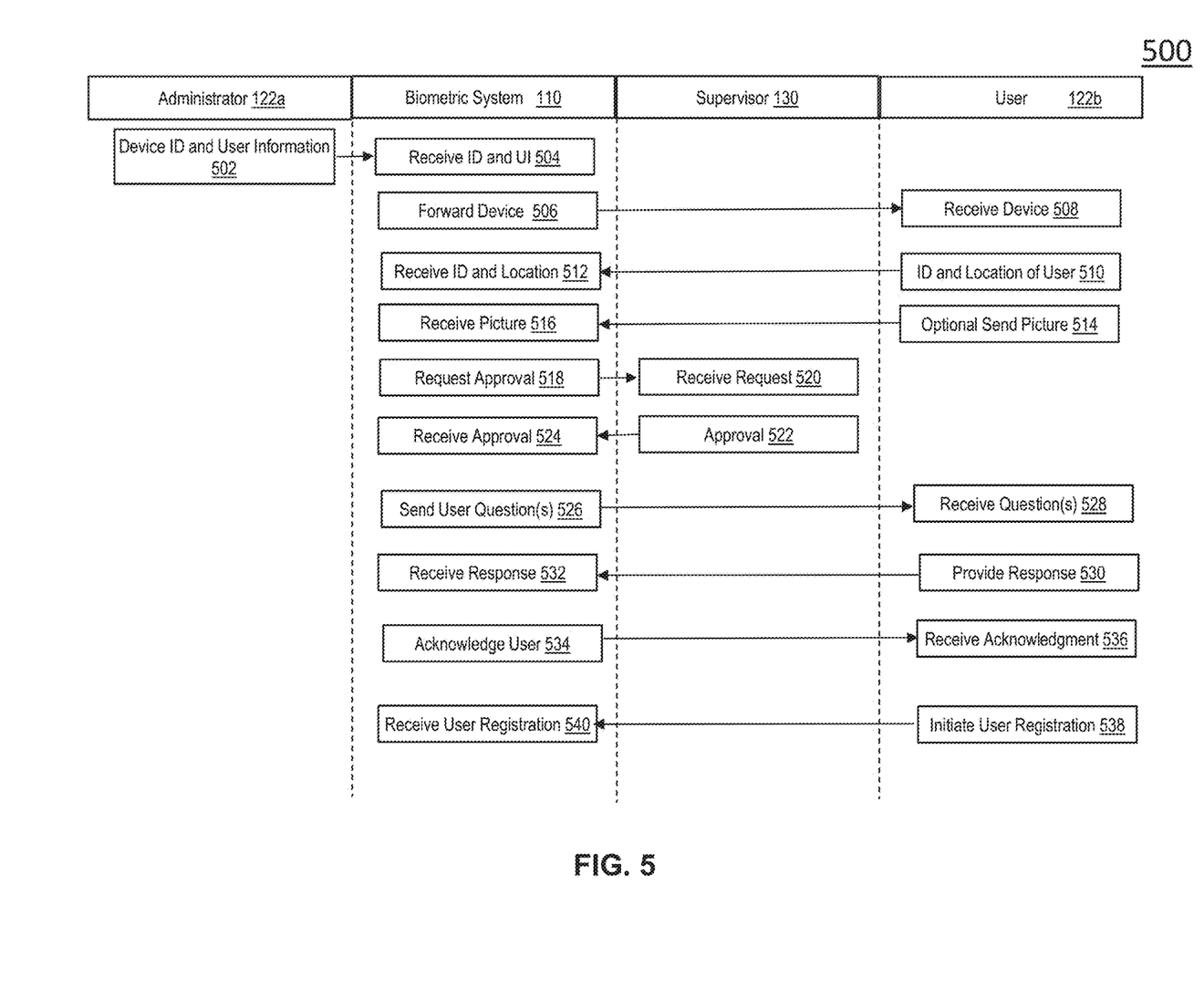
FIG. 5 is a flow chart illustrating a method for securely registering a user in a biometric system in accordance with an embodiment.

FIG. 5 is a flow chart 500 illustrating a method for securely registering a user in a biometric system 110 in accordance with an embodiment. As shown in FIG. 5, in Step 502, the administrator 122a can input the identifier or ID (i.e., 123456) of the biometric device 120 and user information of the user 122b into the biometric system 110. In accordance with an exemplary embodiment, the identifier or ID of the biometric device 120 can be manually input into the biometric system and/or scanned. In accordance with an alternative embodiment, for example, the ID of the biometric device 120 and user information can be input into a client device 124a of the administrator and sent to the biometric system 110. In Step 504, the biometric system 110 records the ID of the biometric device 120 and the user information, for example, in a memory, of the biometric system 110.

In accordance with an exemplary embodiment, upon receiving the ID of the biometric device 120 and the user information of the user 122b, in Step 506, the biometric system 110 will initiate via a postal mail or delivery system to the user 122b. In Step 508, the user 122b receives the biometric device 120. In Step 510, the user 122b sends the ID of the biometric device 120 along with a location of the user 122b, for example, via a client device 124b, to the biometric system 110. For example, the location of the user 122b can be determined, for example, based on a GPS (global positioning system), IP address and/or any other system, which can provide a location of either the biometric device 120 and/or client device 124b, and the user 122b. In Step 512, the ID of the biometric device 120 and the location of the user 122b is received by the biometric system 110, and the biometric system 110 confirms that the information provided in Step 510 matches the information provided by the administrator 122a, for example, in Step 502.

In accordance with another embodiment, in Step 514, the user 122b can provide a photograph or digital image of the user 122b to the biometric system. In Step 516, the photograph or digital image is received by the biometric system 110 and based upon, for example, instructions, received from the administrator 122a, received in Step 502, the biometric system 110 in Step 518 forwards the photograph or digital image, for example, to the supervisor 130 with a request for approval or authorization that the photograph or digital image is of the intended recipient (i.e., user 122b) of the biometric device 120. In Step 520, the supervisor 130 receives the photograph or digital image and in Step 522, if appropriate, approves the request by sending an approval or authorization that the individual in the photograph or digital image to the knowledge of the supervisor 130 is the person or individual is the intended recipient. In Step 524, the biometric system 110 receives the approval from the supervisor 130. In an alternative embodiment, the Step 516, the biometric system 110 can receive the photograph or digital image form the user 122b and based on a facial recognition program or application and a previously submitted image, for example, submitted with the device ID and user information in Step 502 can approve or authorize that the user 122b is the intended user.

In accordance with an exemplary embodiment, in Step 526, the biometric system 110 can also authorize or authenticate the user 122b of the biometric device 120 using one or more questions. In Step 528, the user 122b receives the one or more questions, and in Step 530, the user 122b provides response and/or answers to the one or more questions to the biometric system 110. In Step 532, the biometric system 110 receives the answers and/or responses to the one or more questions, and if the one or more questions are correctly answered and/or responded to, the user 122b can be authenticated or authorized to user the biometric device 120.

In Step 534, the biometric system 110 will initiate the registration process if the user 122b has correctly responded to each of the requests that were sent to and/or received from the user 122b, for example, including ID of the biometric device 120 and location of the user 122b received in Step 512), authorization of photograph or digital image received in Step 516, and/or responses to questions received in Step 532. In Step 536, the user 122b will receive an acknowledgement and request for the user 122b to enter biometric information into the biometric device 120, and in Step 538, the user 122b can begin the registration process of the biometric device 120. In Step 540, the biometric system 540 receives the biometric information of the user 122b. The biometric information of the user 122b can be received by the biometric system 110 directly form the biometric device 120, for example, via NFC (near-field communication) and/or Bluetooth, and/or alternatively, the biometric information can be uploaded into a client device 124b, and sent to the biometric system 110. In accordance with an exemplary embodiment, the biometric device 120 will use an encryption algorithm, for example, Pubic key infrastructure (PKI) to encrypt the biometric data being sent to, for example, the computer processor, of the biometric system 110 for both security and privacy reasons.

Figure 6:
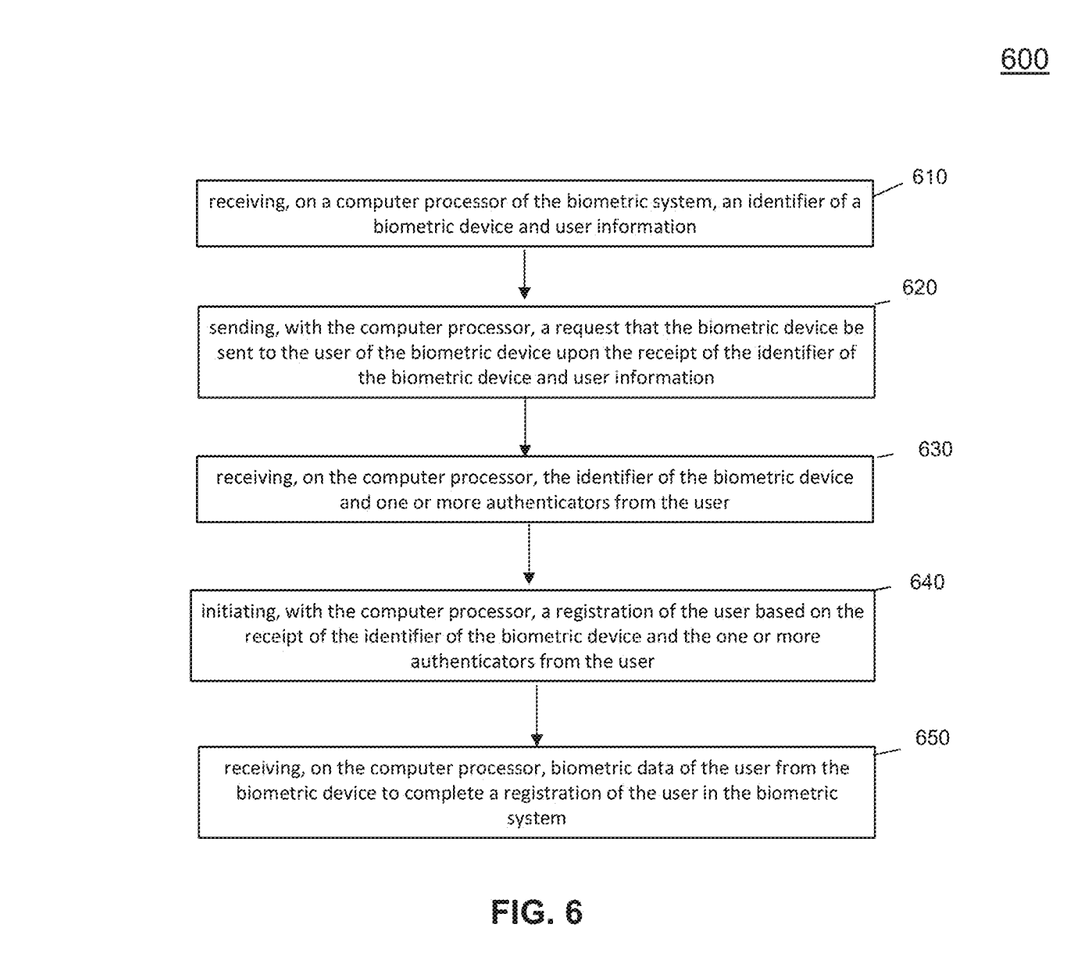
FIG. 6 is another flow chart illustrating a method for securely registering a user in a biometric system in accordance with an embodiment.

FIG. 6 is another flow chart 600 illustrating a method for securely registering a user in a biometric system in accordance with an embodiment. As shown in FIG. 6, in Step 610, an identifier of a biometric device and user information is received on a computer processor of the biometric system. In Step 620, a request that the biometric device be sent to the user of the biometric device is sent upon the receipt of the identifier of the biometric device and user information. In Step 630, the identifier of the biometric device and one or more authenticators from the user are received on the computer processor. In Step 640, a registration of the user based on the receipt of the identifier of the biometric device and the one or more authenticators from the user is initiated. In Step 650, biometric data of the user is received from the biometric device to complete a registration of the user in the biometric system.

Figure 7:
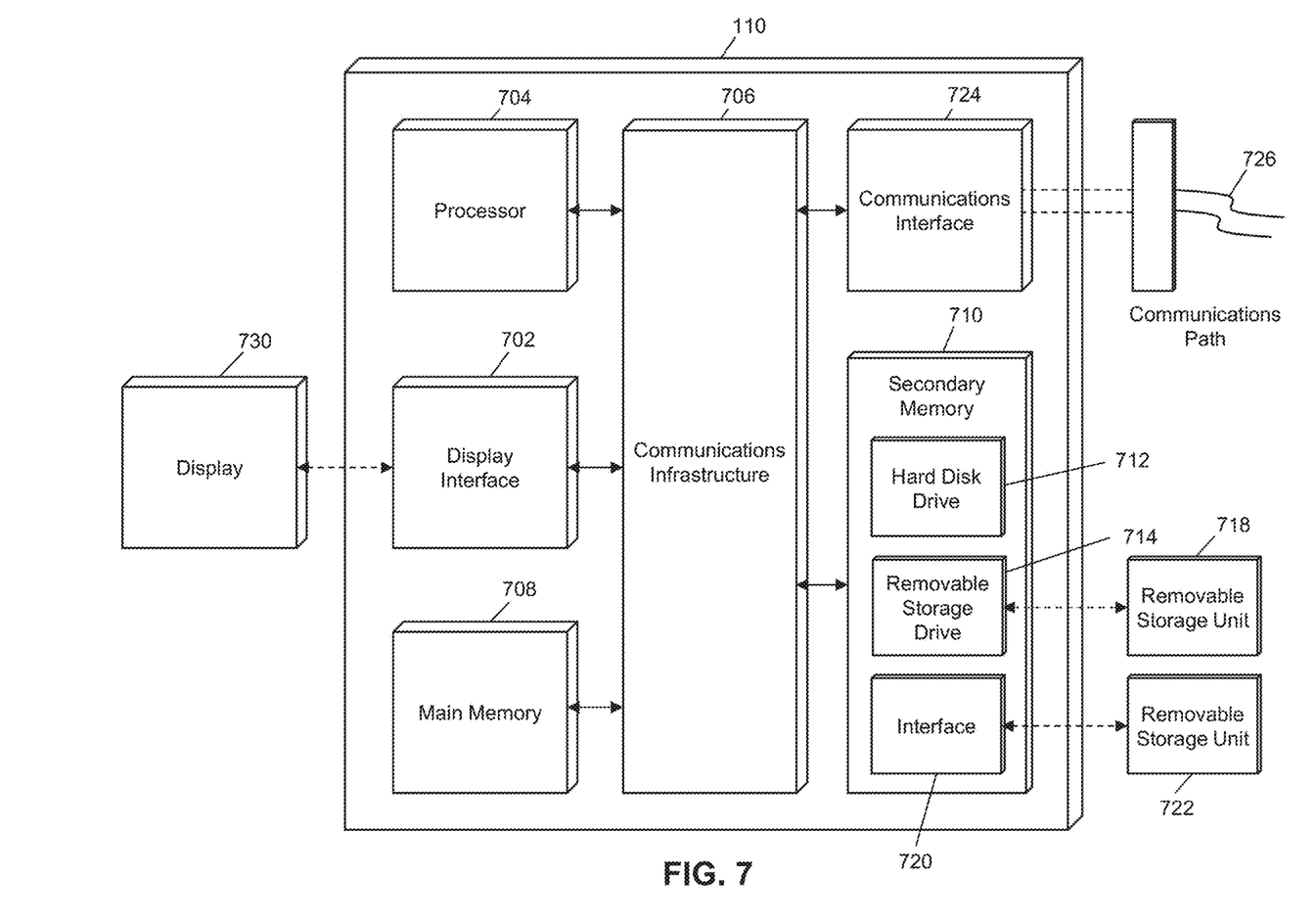
FIG. 7 is a block diagram illustrating a computer system architecture in accordance with exemplary embodiments.

FIG. 7 illustrates a biometric system 110 in which embodiments of the present disclosure, or portions thereof, may be implemented as computer-readable code. For example, the system and methods of FIGS. 4-6 may be implemented in the biometric system 110 using hardware, software, firmware, non-transitory computer readable media having instructions stored thereon, or a combination thereof and may be implemented in one or more computer systems or other processing systems. Hardware, software, or any combination thereof may embody modules and components used to implement the system and methods of FIGS. 4-6.

If programmable logic is used, such logic may execute on a commercially available processing platform configured by executable software code to become a specific purpose computer or a special purpose device (for example, programmable logic array, application-specific integrated circuit, etc.). A person having ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device and a memory may be used to implement the above described embodiments.

A processor unit or device (i.e., computer processor) as discussed herein may be a single processor, a plurality of processors, or combinations thereof. Processor devices may have one or more processor "cores." The terms "computer program medium," "non-transitory computer readable medium," and "computer usable medium" as discussed herein are used to generally refer to tangible media such as a removable storage unit 718, a removable storage unit 722, and a hard disk installed in hard disk drive 712.

Various embodiments of the present disclosure are described in terms of this example biometric system 110. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Processor device (or computer processor) 704 may be a special purpose or a general purpose processor device specifically configured to act as a special purpose computer to perform the functions discussed herein. The processor device 704 may be connected to a communications infrastructure 706, such as a bus, message queue, network, multi-core message-passing scheme, etc. The network may be any network suitable for performing the functions as disclosed herein and may include a local area network (LAN), a wide area network (WAN), a wireless network (for example, WiFi), a mobile communication network, a satellite network, the Internet, fiber optic, coaxial cable, infrared, radio frequency (RF), or any combination thereof. Other suitable network types and configurations will be apparent to persons having skill in the relevant art. The biometric system 110 may also include a main memory 708 (for example, random access memory, read-only memory, etc.), and may also include a secondary memory 710. The secondary memory 710 may include the hard disk drive 712 and a removable storage drive 714, such as a floppy disk drive, a magnetic tape drive, an optical disk drive, a flash memory, etc.

The removable storage drive 714 may read from and/or write to the removable storage unit 718 in a well-known manner. The removable storage unit 718 may include a removable storage media that may be read by and written to by the removable storage drive 714. For example, if the removable storage drive 714 is a floppy disk drive or universal serial bus port, the removable storage unit 718 may be a floppy disk or portable flash drive, respectively. In one embodiment, the removable storage unit 718 may be non-transitory computer readable recording media.

In some embodiments, the secondary memory 710 may include alternative means for allowing computer programs or other instructions to be loaded into the biometric system 110, for example, the removable storage unit 722 and an interface 720. Examples of such means may include a program cartridge and cartridge interface (for example, as found in video game systems), a removable memory chip (for example, EEPROM, PROM, etc.) and associated socket, and other removable storage units 722 and interfaces 720 as will be apparent to persons having skill in the relevant art.

Data stored in the biometric system 110 (for example, in the main memory 1008 and/or the secondary memory 710) may be stored on any type of suitable computer readable media, such as optical storage (for example, a compact disc, digital versatile disc, Blu-ray disc, etc.) or magnetic tape storage (for example, a hard disk drive). The data may be configured in any type of suitable database configuration, such as a relational database, a structured query language (SQL) database, a distributed database, an object database, etc. Suitable configurations and storage types will be apparent to persons having skill in the relevant art.

The biometric system 110 may also include a communications interface 724. The communications interface 724 may be configured to allow software and data to be transferred between the biometric system 110 and external devices. Exemplary communications interfaces 724 may include a modem, a network interface (for example, an Ethernet card), a communications port, a PCMCIA slot and card, etc. Software and data transferred via the communications interface 724 may be in the form of signals, which may be electronic, electromagnetic, optical, or other signals as will be apparent to persons having skill in the relevant art. The signals may travel via a communications path 726, which may be configured to carry the signals and may be implemented using wire, cable, fiber optics, a phone line, a cellular phone link, a radio frequency link, etc.

The biometric system 110 may further include a display interface 702. The display interface 702 may be configured to allow data to be transferred between the biometric system 110 and external display 730. Exemplary display interfaces 702 may include high-definition multimedia interface (HDMI), digital visual interface (DVI), video graphics array (VGA), etc. The display 730 may be any suitable type of display for displaying data transmitted via the display interface 702 of the biometric system 110, including a cathode ray tube (CRT) display, liquid crystal display (LCD), light-emitting diode (LED) display, capacitive touch display, thin-film transistor (TFT) display, etc.

Computer program medium and computer usable medium may refer to memories, such as the main memory 708 and secondary memory 710, which may be memory semiconductors (for example, DRAMs, etc.). These computer program products may be means for providing software to the biometric system 110. Computer programs (for example, computer control logic) may be stored in the main memory 708 and/or the secondary memory 710. Computer programs may also be received via the communications interface 724. Such computer programs, when executed, may enable biometric system 110 to implement the present methods as discussed herein. In particular, the computer programs, when executed, may enable processor device 704 to implement the system and methods illustrated by FIGS. 4-6, as discussed herein. Accordingly, such computer programs may represent controllers of the biometric system 110. Where the present disclosure is implemented using software, the software may be stored in a computer program product and loaded into the biometric system 110 using the removable storage drive 714, interface 720, and hard disk drive 712, or communications interface 724.

The processor device 704 may comprise one or more modules or engines configured to perform the functions of the biometric system 110. Each of the modules or engines may be implemented using hardware and, in some instances, may also utilize software, such as corresponding to program code and/or programs stored in the main memory 708 or secondary memory 710. In such instances, program code may be compiled by the processor device 704 (for example, by a compiling module or engine) prior to execution by the hardware of the biometric system 110. For example, the program code may be source code written in a programming language that is translated into a lower level language, such as assembly language or machine code, for execution by the processor device 704 and/or any additional hardware components of the biometric system 110. The process of compiling may include the use of lexical analysis, preprocessing, parsing, semantic analysis, syntax-directed translation, code generation, code optimization, and any other techniques that may be suitable for translation of program code into a lower level language suitable for controlling the biometric system 110 to perform the functions disclosed herein. It will be apparent to persons having skill in the relevant art that such processes result in the biometric system 110 being a specially configured biometric system 110 uniquely programmed to perform the functions discussed above.

In accordance with an exemplary embodiment, the biometric system 110 can be a multi-function printer (MFP), an imaging forming apparatus, a printer or a printing device having, for example, a card reader or other system, which requires a user to be authorized to access print, fax, scan and/or copy functions. The multi-function printer (MFP), imaging forming apparatus can carry out various image processing under the control of a print controller or CPU, and sends the processed print image data to the print engine. The image processing section can also include a scanner section (scanner engine) for optically reading a document, such as an image recognition system. The scanner section receives the image from the scanner engine and converts the image into a digital image. The print engine forms an image on a print media (or recording sheet) based on the image data sent from the image processing section. The central processing unit (CPU) (or processor) and the memory can include a program for RIP processing (Raster Image Processing), which is a process for converting print data included in a print job into Raster Image data to be used in the printer or print engine.

In accordance with an exemplary embodiment, the operation of printer section commences when the printer section receives a page description via the network I/F in the form of a print job data stream and/or fax data stream. The page description may be any kind of page description languages (PDLs), such as PostScript® (PS), Printer Control Language (PCL), Portable Document Format (PDF), and/or XML Paper Specification (XPS). Examples of the multi-function printer (MFP), imaging forming apparatus, the printer or the printing device consistent with exemplary embodiments of the disclosure include, but are not limited to, a multi-function peripheral (MFP), a laser beam printer (LBP), an LED printer, a multi-function laser beam printer including copy function.

Figure 8:
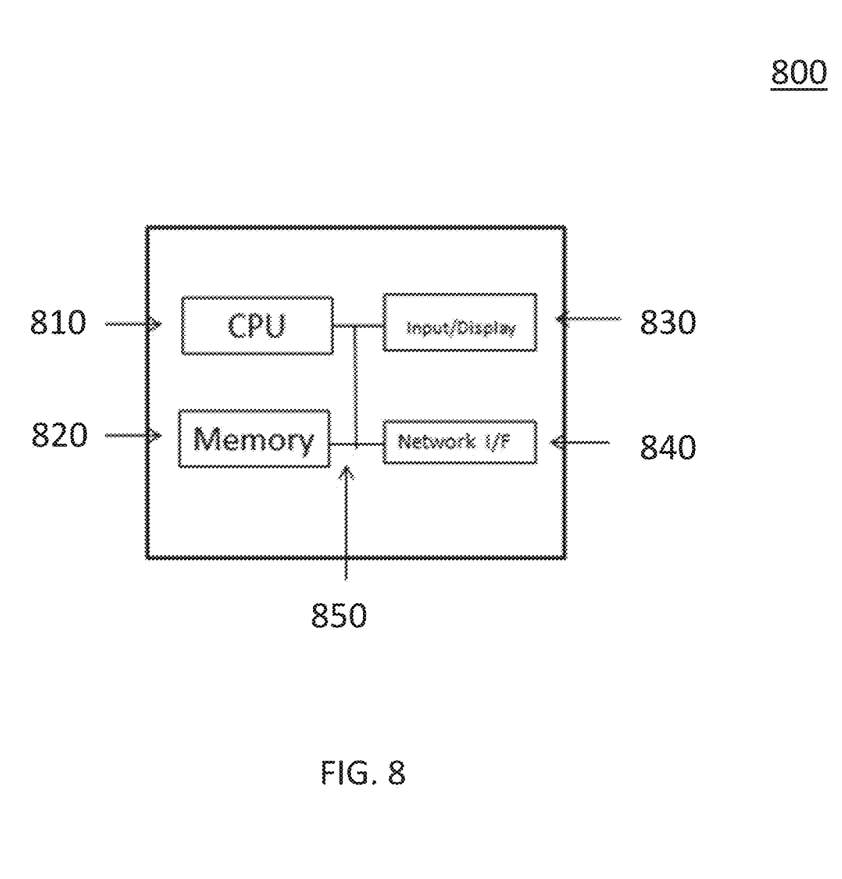
FIG. 8 is an illustration of a biometric device in accordance with an exemplary embodiment.

FIG. 8 is an illustration of a biometric device 120 in accordance with an exemplary embodiment. In accordance with an exemplary embodiment, the exemplary biometric device 120 is a security identification and authentication device, which uses automated methods of verifying or recognizing the identity of a living person based on a physiological or behavioral characteristic. The method of recognizing the user can include, for example, fingerprints, electrocardiogram (ECG or EKG) information, facial images, iris, and voice recognition. For example, in accordance with an exemplary embodiment, the biometric device 120 is a wearable device, for example, a Nymi™ band, which detection of the user is based on the electrocardiogram (ECG) and its unique properties, i.e., electrical activity of the heartbeat of the wearer.

As shown in FIG. 8, the biometric device 120 can include a processor or central processing unit (CPU) 810, and one or more memories 820 for storing software programs and data, for example, an operating system. In accordance with an exemplary embodiment, the processor or CPU 810 carries out the instructions of a computer program, which operates and/or controls at least a portion of the functionality of the biometric device 120. The biometric device 120 can also include an input unit and/or display unit or graphical user interface (GUI) 830, and a network interface (I/F) 840, which is configured to connect the biometric device 120 to the biometric system 110 via, for example, a wire or wireless technology, for example, Bluetooth. A bus 850 can connect the various components 810, 820, 830, 840, within the biometric device 120.

In accordance with an exemplary embodiment, the methods and processes as disclosed can be implemented on a non-transitory computer readable medium. The non-transitory computer readable medium may be a magnetic recording medium, a magneto-optic recording medium, or any other recording medium which will be developed in future, all of which can be considered applicable to the present invention in all the same way. Duplicates of such medium including primary and secondary duplicate products and others are considered equivalent to the above medium without doubt. Furthermore, even if an embodiment of the present invention is a combination of software and hardware, it does not deviate from the concept of the invention at all. The present disclosure may be implemented such that its software part has been written onto a recording medium in advance and will be read as required in operation.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional examples that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

It will be apparent to those skilled in the art that various modifications and variation can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for securely registering a user in a biometric system, the method comprising:
   receiving, on a computer processor of the biometric system, an identifier of a biometric device and user information;
   sending, with the computer processor, a request that the biometric device be sent to the user of the biometric device upon the receipt of the identifier of the biometric device and user information;
   receiving, on the computer processor, the identifier of the biometric device and one or more authenticators from the user;
   initiating, with the computer processor, a registration of the user based on the receipt of the identifier of the biometric device and the one or more authenticators from the user; and
   receiving, on the computer processor, biometric data of the user from the biometric device to complete a registration of the user in the biometric system.

2. The method according to claim 1, wherein the one or more authenticators include a location of the user, a digital image of the user, and one or more responses to questions based on the user information.

3. The method according to claim 2, further comprising initiating the registration of the user only wherein the one or more of the location of the user, the digital image of the user, and/or the one or more responses to questions based on the user information matches a location of the user, a digital image of the user, and/or one more questions based on the user information.

4. The method according to claim 1, wherein the one or more authenticators includes a location of the user, the method comprising:
   receiving, on the computer processor, a location of the user; and
   confirming, with the computer processor, that the location of the user matches a location of the user in the user information.

5. The method according to claim 4, further comprising:
   receiving the location of the user from a global positioning system, the global positioning system being received from a mobile client of the user or IP address of a client device.

6. The method according to claim 1, wherein the one or more authenticators includes a digital image of the user, the method comprising:
   receiving, on the computer processor, the digital image;
   forwarding, by the computer processor, the digital image to a third party for confirmation that the digital image is the user; and
   receiving, on the computer processor, confirmation form the third party that the digital image is the user.

7. The method according to claim 1, wherein the one or more authenticators is one or more questions, each of the one or more questions being generated based on the user information, the method comprising:
   sending, by the computer processor, the each of the one or more questions to the user;
   receiving, by the computer processor, a response to the each of the one or more questions; and
   confirming, by the computer processor, that each response to the each of the or more questions is correctly answered.

8. The method according to claim 7, further comprising:
   setting a time limit for the user to provide the response to each of the one or more questions.

9. The method according to claim 1, wherein the biometric device is a wearable biometric device, the method comprising:
   exchanging the biometric data of the user with the computer processor of the biometric system via a Bluetooth and/or a Near Field Communication.

10. The method according to claim 1, wherein the biometric system is a computer, a card reader, a software application, a database, and/or a file.

11. The method according to claim 1, wherein biometric device is a wearable biometric device configured to measure electrical activity of a heartbeat of the user.

12. The method according to claim 1, further comprising:
    receiving, by the computer processor, encrypted biometric data of the user during the completion of the registration of the user in the biometric system.

13. A non-transitory computer readable medium storing computer readable program code executed by a processor for securely registering a user in a biometric system, the process comprising:
    receiving, on a computer processor of the biometric system, an identifier of a biometric device and user information;
    sending, with the computer processor, a request that the biometric device be sent to the user of the biometric device upon the receipt of the identifier of the biometric device and user information;
    receiving, on the computer processor, the identifier of the biometric device and one or more authenticators from the user;
    initiating, with the computer processor, a registration of the user based on the receipt of the identifier of the biometric device and the one or more authenticators from the user; and
    receiving, on the computer processor, biometric data of the user from the biometric device to complete a registration of the user in the biometric system.

14. The non-transitory computer readable medium according to claim 13, wherein the one or more authenticators include a location of the user, a digital image of the user, and one or more responses to questions based on the user information.

15. A system for securely registering a user in a biometric system, the system comprising:
    a biometric device;
    a computer processor of the biometric system, the computer processor configured to:
       receive an identifier of the biometric device and user information;
       send a request that the biometric device be sent to the user of the biometric device upon the receipt of the identifier of the biometric device and user information;
       receive the identifier of the biometric device and one or more authenticators from the user;
       initiate a registration of the user based on the receipt of the identifier of the biometric device and the one or more authenticators from the user; and
       receive biometric data of the user from the biometric device to complete a registration of the user in the biometric system.

16. The system according to claim 15, wherein the one or more authenticators include a location of the user, a digital image of the user, and one or more responses to questions based on the user information.

17. The system according to claim 16, wherein the computer processor is configured to:

initiate the registration of the user only wherein the one or more of the location of the user, the digital image of the user, and/or the one or more responses to questions based on the user information matches a location of the user, a digital image of the user, and/or one more questions based on the user information.

18. The system according to claim 15, wherein the one or more authenticators includes a location of the user, and the computer processor is configured to:

receive a location of the user; and confirm that the location of the user matches a location of the user in the user information.

19. The system according to claim 15, wherein the one or more authenticators includes a digital image of the user, the computer processor configured to:

receive the digital image;

forward the digital image to a third party for confirmation that the digital image is the user; and receive confirmation form the third party that the digital image is the user.

20. The system according to claim 15, wherein the one or more authenticators is one or more questions, each of the one or more questions being generated based on the user information, the computer processor configured to:

send the each of the one or more questions to the user;

receive a response to the each of the one or more questions; and confirm that each response to the each of the or more questions is correctly answered.

* * * * *